(12) United States Patent
Kuebler et al.

(10) Patent No.: US 10,016,300 B2
(45) Date of Patent: Jul. 10, 2018

(54) HANDPIECE FOR THE PHACOEMULSIFICATION OF AN EYE LENS

(71) Applicant: Carl Zeiss Meditec AG, Jena (DE)

(72) Inventors: Christoph Kuebler, Oberkochen (DE); Wolfram Wehner, Nuremberg (DE); Karlheinz Rein, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 521 days.

(21) Appl. No.: 14/671,917

(22) Filed: Mar. 27, 2015

(65) Prior Publication Data

US 2015/0196426 A1    Jul. 16, 2015

Related U.S. Application Data

(63) Continuation of application No. PCT/EP2013/002805, filed on Sep. 18, 2013.

(30) Foreign Application Priority Data

Sep. 28, 2012  (DE) .......................... 10 2012 019 165

(51) Int. Cl.
*A61B 17/20* (2006.01)
*A61F 9/007* (2006.01)
*A61M 1/00* (2006.01)

(52) U.S. Cl.
CPC ...... *A61F 9/00745* (2013.01); *A61F 9/00736* (2013.01); *A61M 1/0039* (2013.01); *A61F 2250/0093* (2013.01); *A61M 2205/058* (2013.01); *A61M 2210/0612* (2013.01)

(58) Field of Classification Search
CPC .............. A61F 9/00745; A61F 9/00736; A61F 2250/0093; A61M 1/0039; A61M 2205/058; A61M 2210/0612
See application file for complete search history.

(56) References Cited

U.S. PATENT DOCUMENTS

| 5,651,783 A * | 7/1997 | Reynard | ................ A61B 1/042 |
| | | | 606/17 |
| 2001/0031951 A1* | 10/2001 | Pezzola | ............... A61F 9/00745 |
| | | | 604/275 |
| 2009/0005712 A1* | 1/2009 | Raney | .............. A61B 17/32006 |
| | | | 601/2 |

(Continued)

FOREIGN PATENT DOCUMENTS

WO   2010/094353 A1   8/2010

OTHER PUBLICATIONS

International Search Report dated Nov. 12, 2013 of international application PCT/EP2013/002805 on which this application is based.

(Continued)

*Primary Examiner* — Kevin C Sirmons
*Assistant Examiner* — Leah Swanson
(74) *Attorney, Agent, or Firm* — Walter Ottesen, P.A.

(57) ABSTRACT

The invention relates to a handpiece for the phacoemulsification of an eye lens, having a needle with an aspiration line arranged therein for transporting an aspiration fluid and at least one drive element for generating a longitudinal wave, wherein the drive element is arranged in such a way that the longitudinal wave can be coupled directly into the aspiration fluid.

9 Claims, 4 Drawing Sheets

(56) References Cited

U.S. PATENT DOCUMENTS

2010/0094321 A1 4/2010 Akahoshi et al.
2011/0218483 A1 9/2011 Hunter
2013/0237900 A1 9/2013 Hauger
2013/0261637 A1 10/2013 Kuebler et al.

OTHER PUBLICATIONS

English translation of the Office action of the German Patent Office dated Dec. 18, 2012 in German patent application 10 2012 019 165.0 on which the claim of priority is based.
Translation of International Preliminary Report on Patentability and Written Opinion dated Apr. 9, 2015 of international application PCT/EP2013/002805 on which this application is based.

* cited by examiner

HANDPIECE FOR THE PHACOEMULSIFICATION OF AN EYE LENS

CROSS REFERENCE TO RELATED APPLICATIONS

This application is a continuation application of international patent application PCT/EP2013/002805, filed Sep. 18, 2013, designating the United States and claiming priority from German application 10 2012 019 165.0, filed Sep. 28, 2012, and the entire content of both applications is incorporated herein by reference.

FIELD OF THE INVENTION

The invention relates to a handpiece for the phacoemulsification of an eye lens.

BACKGROUND OF THE INVENTION

There are a number of surgical techniques for treating clouding within the eye lens, which is referred to as a cataract in medicine. The most common technique is phacoemulsification, in which a thin needle is introduced into the eye lens and excited to vibrate via ultrasound. The vibrating needle emulsifies the lens in its direct vicinity in such a way that the created lens particles can be suctioned away through an aspiration line via a pump. In the process, a rinsing fluid (irrigation fluid) is supplied, with the particles and the fluid being suctioned away through the aspiration line, which is usually arranged within the needle. Once the lens has been completely emulsified and removed, a new artificial lens can be inserted into the empty capsular bag, and so a patient treated thus can regain good visual acuity.

During the emulsification of the eye lens via ultrasound, the vibrating needle and a sleeve surrounding the needle rub at the tissue of the eye to be treated, and so there can be strong heating of the contact region. In the case of relatively long operation of the vibrating needle, the tissue region around the needle can burn. Since the needle is punched through the cornea, this means that the cornea in particular is subject to a very large thermal load. Even an only locally burnt cornea is classified as a grave complication, which must be avoided at all costs.

United States patent application publication 2013/0237900 discloses a control device for an ophthalmic surgical system, which has a measuring device for establishing the volume of an anterior chamber of the eye of an eye to be treated during a phacoemulsification and a control unit which calculates a controlled variable as a function of the established volume of the anterior chamber of the eye. A pressure or a volume flow in an irrigation line and/or aspiration line of the ophthalmic surgical system can be controlled via the controlled variable.

United States patent application publication 2011/0218483 A1 discloses a phacoemulsification handpiece which has a needle and, coupled thereon, a microelectromechanical system (MEMS). Furthermore, the handpiece can have a horn, wherein the horn is coupled to the needle and the MEMS. The MEMS is configured in such a way that it can generate a movement of the needle in at least one direction.

United States patent application publication 2010/0094321 A1 discloses an ultrasound handpiece for the phacoemulsification, which has at least one pair of vibrating piezo-elements that are arranged within the handpiece in such a way that they generate vibrations which are oriented perpendicular, or inclined at an angle, to the longitudinal axis of the handpiece.

SUMMARY OF THE INVENTION

It is an object of the invention to develop a handpiece for the phacoemulsification, via which an emulsification of the lens with only little, or even no, thermal load on the eye can be achieved, even during a relatively long operation duration.

This object is achieved by a handpiece for the phacoemulsification of an eye lens according to the invention having:
a needle with an aspiration line arranged therein for transporting an aspiration fluid and
at least one drive element for generating a longitudinal wave,
wherein the drive element is arranged in such a way that the longitudinal wave can be coupled directly into the aspiration fluid.

In handpieces in accordance with the prior art, the drive element causes the longitudinal wave generated thereby to be used entirely for moving the needle. The longitudinal wave is generated at a high frequency, for example, with a resonant frequency of the drive element at approximately 40 000 Hz, such that the needle thus made to vibrate is used for comminuting the eye lens in the region of the distal end of the needle. By contrast, in the handpiece according to the invention, the longitudinal wave generated by a drive element can be coupled directly into the aspiration fluid. The kinetic energy of the vibrating element transmitted by the longitudinal wave is therefore used to generate a fluid pressure which brings about comminuting of the eye lens to be treated. Using this, the energy emitted by the drive element is transmitted through the aspiration fluid such that no, or only little, energy, for example, 30% of the energy, is available for movement of the needle. Consequently, no, or only little, kinetic energy is converted into frictional heat in the surroundings of the needle, and so there can be no temperature load on the tissue surrounding the needle.

Preferably, the whole energy emitted by the drive element can be coupled into the aspiration fluid such that the needle remains completely stationary during the phacoemulsification. Since there consequently no longer is any relative movement between the needle and the tissue surrounding the needle, there also is no heating in the surrounding tissue. The energy emitted by the drive element in the form of longitudinal waves then is only transported via aspiration fluid as far as the distal end of the needle to the eye lens to be treated. Therefore, a very high degree of effectiveness is achieved.

In general, there is no trauma or destruction of sensitive tissue in regions of the eye that are not the distal end of the needle as a result of the handpiece according to the invention. This is advantageous, particularly in the case of a blockage (occlusion) of the aspiration line. In this case, energy is no longer emitted into the tissue surrounding the needle and not emitted to the surroundings of the distal end of the needle either. All longitudinal waves only reach as far as the lens particle blocking the aspiration line. Thus, the energy is only effective where it is actually required.

In accordance with a preferred embodiment of the invention, the drive element is arranged within the aspiration line and it can be brought into direct contact with the aspiration fluid. Then, a very simple structure can be achieved, in which no damping losses are created as a result of interspersed elements. The effectiveness of the handpiece is once again increased by such a setup.

The drive element preferably has piezoelectric elements. As a result, high frequencies of up to 40 000 Hz are possible, wherein a skillful arrangement of the piezoelectric elements renders relatively long travels for the longitudinal movement possible.

The drive element preferably has a ring-shaped embodiment. Consequently, the aspiration fluid to be suctioned away can be discharged through the central recess formed by the ring. Therefore, starting from the distal end of the needle, the aspiration fluid need not be discharged via detours, but can be guided centrally through the whole handpiece. As a result, a simple and space-saving structure is possible.

Preferably, the needle has a funnel-shaped region with a tapering end, which is oriented toward the distal end of the needle. As a result of a funnel-shaped region, the longitudinal waves can reach a higher speed in the direction toward the tapering end, and so a higher sound pressure level can be present at the distal end of the needle.

In the cross section, the funnel-shaped region can have an internal wall contour which is curved toward the central axis of the aspiration line in such a way that an associated center of curvature is oriented toward the tapering end of the funnel-shaped region. By way of such a structure, a particularly strong concentration of the energy emitted by the drive element in the direction of the central axis of the aspiration line is possible, wherein, additionally, a higher wave propagation speed is achieved. This leads to a relatively high sound pressure being able to be present at the distal end of the needle.

In the handpiece according to the invention, the needle can have an internal diameter of 0.4 to 1.1 mm at the distal end thereof. In the case of such a diameter, good aspiration of the generated lens particles and of the fluid still is possible, wherein, at the same time, only a very small incision into the anterior chamber of the eye is required. This means a more sparing surgical intervention, a lower risk of an additional visual disorder such as astigmatism, a faster reestablishment of vision, better optical treatment results and, in general, faster healing and recovery of an operated-on eye.

Preferably, the distal end of the needle is formed from a polymer plastic. Since the needle in the handpiece according to the invention no longer needs to vibrate and no longer needs to achieve mechanical comminuting with the distal end thereof, the requirements in respect of mechanical stability of the needle material are significantly lower than in handpieces in accordance with the prior art. Thus, it is possible for the needle to be formed from a cost-effective polymer plastic, which, for example, is only provided for single use. As a result, a very high level of sterility and a state of the needle which is always perfect can be achieved. A single use is also advantageous in that the tip of the needle can hardly still be worn out during a conventional operation duration. If needles are used a number of times, as is the case in conventional handpieces, the tip of the needle becomes ever rounder with increasing use duration, and so it becomes blunt. As a result, the effectiveness of the phacoemulsification is reduced, and so the needle in conventional handpieces must be excited to vibrate even more strongly in order to achieve an acceptable emulsification of the eye lens. Such a disadvantage can be avoided by the single use of the needle in the handpiece according to the invention.

The polymer plastic can also be a soft polymer plastic which can adapt well to the slit-shaped wound in the case of an incision. As a result, even better sealing is possible and damage to the tissue as a result of the large tensile or compressive stress is avoided. The high degree of sealing is advantageous in that less fluid needs to be pumped through the eye during an operation, and so trauma induced by an operation can be reduced.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
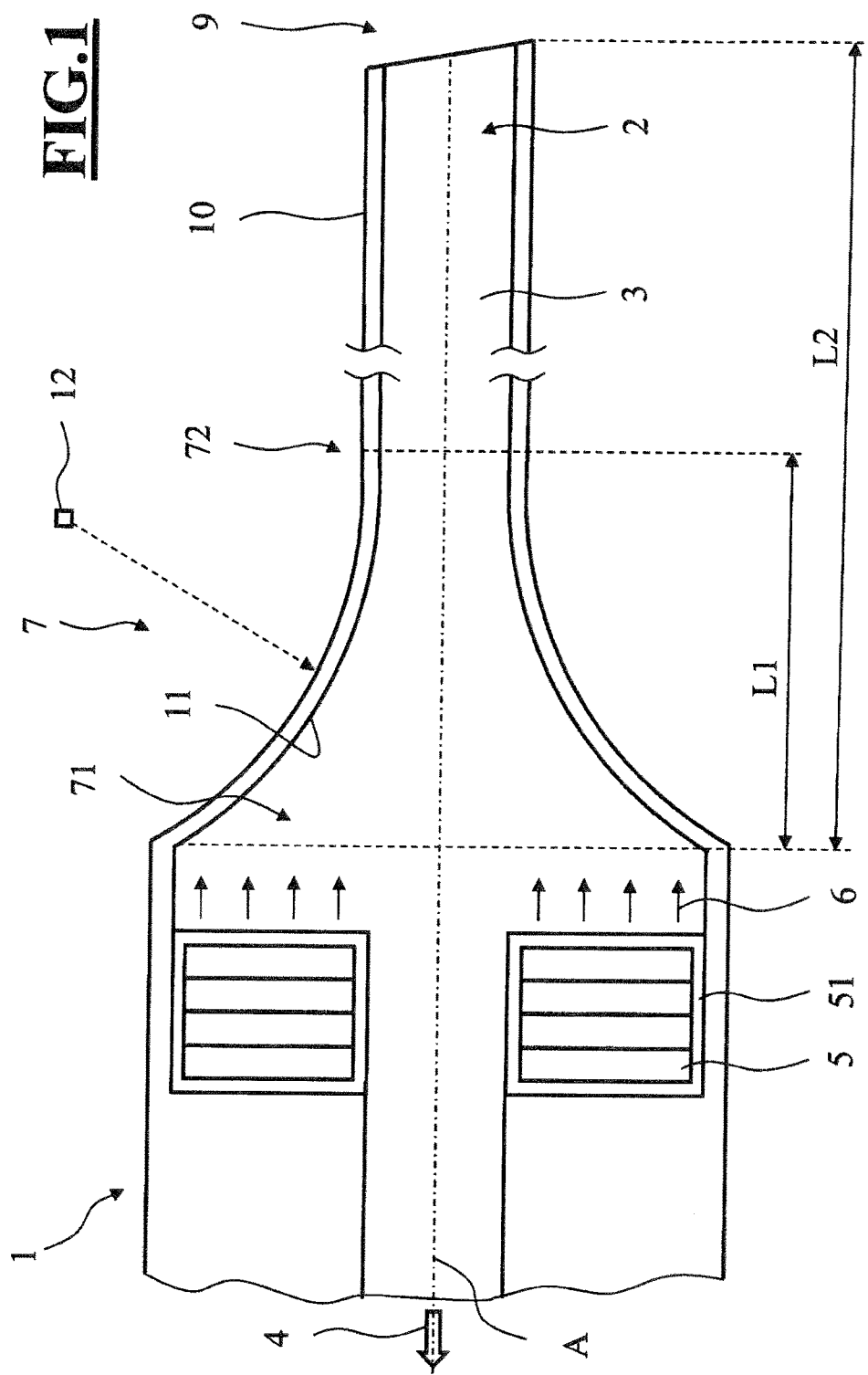
FIG. 1 is a schematic cross-sectional view of a first embodiment of a handpiece according to the invention.

FIG. 1 shows a handpiece 1 in accordance with a first embodiment of the invention. The handpiece 1 has a needle 10 with an aspiration line 2 for transporting aspiration fluid 3, which can be suctioned together with lens particles at a distal end 9 of the needle 10. Here, suctioning away from the distal end 9 of the needle 10 takes place into the handpiece in the direction of the arrow 4. The handpiece 1 furthermore has a drive element 5, which is arranged within the aspiration line. In the embodiment depicted in FIG. 1, the drive element 5 has four piezoelectric elements, which are directly connected to one another. Such a drive element 5 is provided with an electrical insulation 51 such that there can be no short circuit by way of the aspiration fluid.

The drive element 5 can be actuated in such a way that a longitudinal movement is generated in the direction of the arrows 6. The movement energy emitted by the drive element 5 generates a longitudinal wave, which is directly coupled into the aspiration fluid. What is important here is that, in this embodiment of the handpiece, the drive element cannot transfer its kinetic energy to the needle, but only to the aspiration fluid. Consequently, the needle remains stationary without movement, and so only the aspiration fluid can transport the energy to the distal end 9 of the needle 10.

The energy emitted by the drive element 5 can be concentrated particularly well if the aspiration fluid is guided into a funnel-shaped region 7. In this first embodiment depicted in FIG. 1, the aspiration fluid, starting from the drive element 5, reaches an opening zone 71 of the funnel-shaped region 7, whereupon the cross section of the funnel-shaped region 7 increasingly tapers in the direction toward the distal end 9 of the needle 10, until, finally, an end 72 of the funnel-shaped region 7 is reached. In the embodiment depicted in FIG. 1, the funnel-shaped region 7 has a length L1. Starting from the end 72 of the funnel-shaped region 7, the needle 10 is continued in the form of a hollow cylinder. The overall length of the needle 10 including the funnel-shaped region 7 has a length L2. Preferably, the length L1=10 mm and the length L2=50 mm.

A particularly high concentration of the energy emitted by the drive element 5 can be achieved if, in the cross section, the funnel-shaped region 7 has an internal wall contour 11 which is curved toward the central axis A of the aspiration line 2 in such a way that an associated center of curvature 12 is oriented toward the end 72 of the funnel-shaped region 7.

Figure 2:
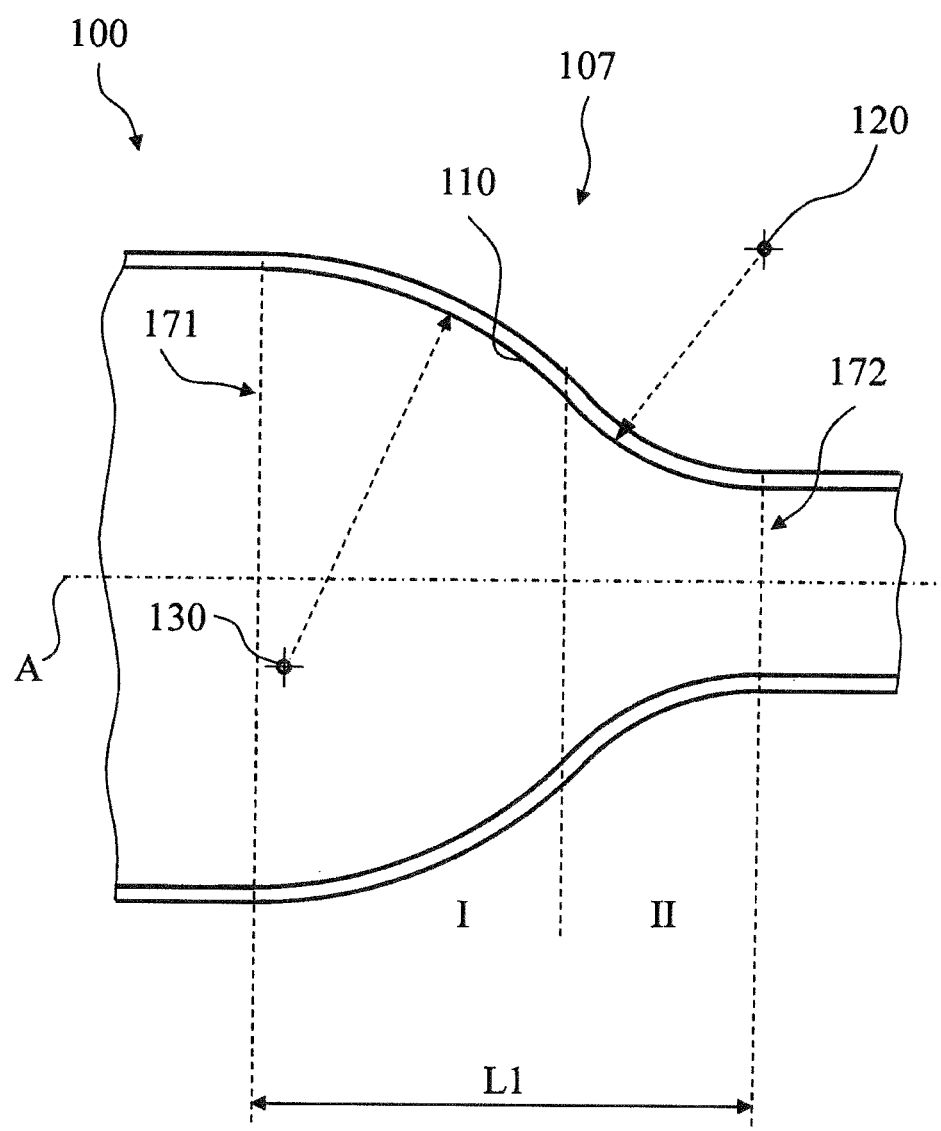
FIG. 2 is a schematic cross-sectional view of a second embodiment of the handpiece according to the invention.

FIG. 2 shows a second embodiment of a front part of the handpiece according to the invention. This handpiece also has a funnel-shaped region, see reference sign 107, which has a first zone I and a second zone II. Here, the second zone II is formed analogously to the funnel-shaped region 7 in accordance with FIG. 1 by virtue of this region 7 having an internal contour which is oriented toward the central axis A of the aspiration line 2 in such a way that an associated center of curvature 120 is oriented toward an end 172 of the funnel-shaped region 107. However, the first zone I is configured in such a way that a center of curvature 130 associated therewith is arranged on an opposite side in relation to the position of the center of curvature 120 of the second zone II. Therefore, the center of curvature 130 is not oriented toward the tapering end 172 of the funnel-shaped region 107, but rather in a direction toward an opening zone 171 of the funnel-shaped region 107, wherein the opening zone 171 is arranged opposite to the end 172 of the funnel-shaped region 107.

Figure 3:
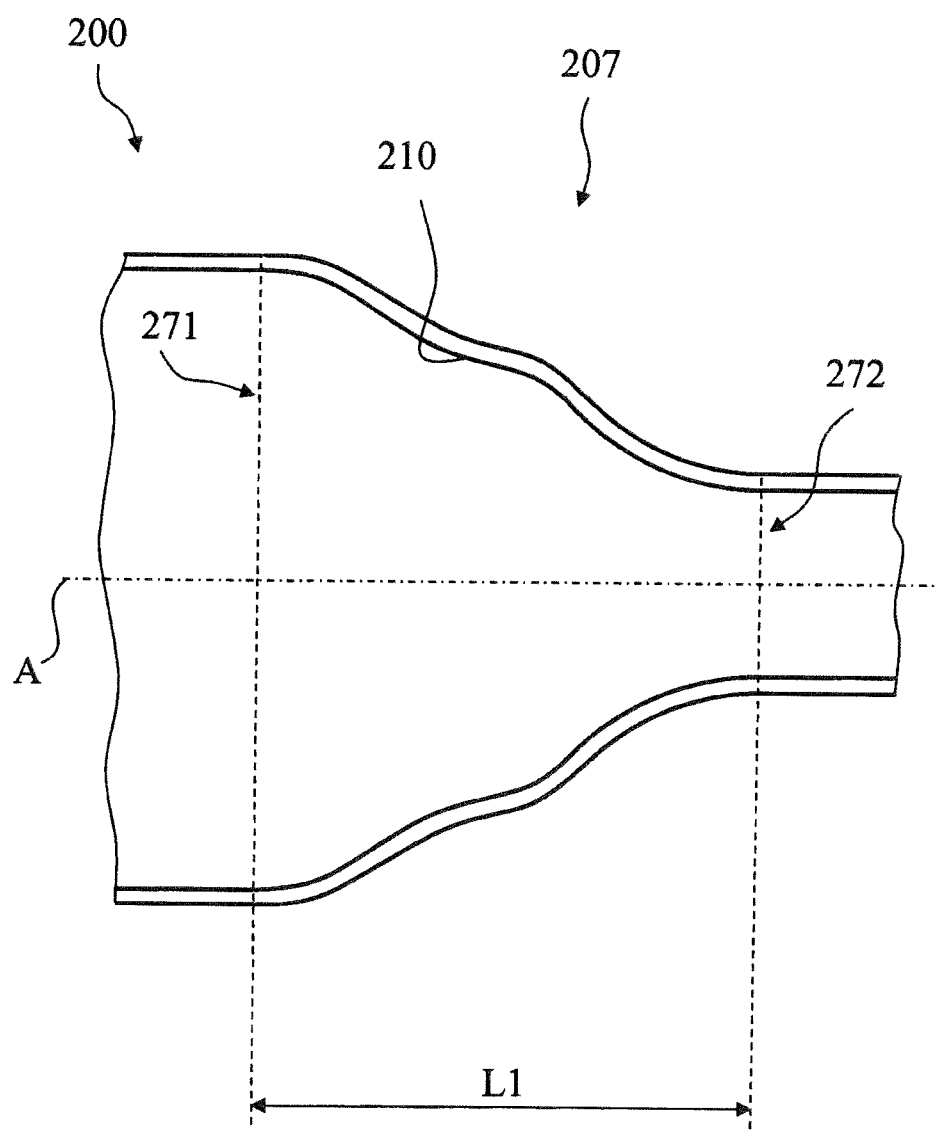
FIG. 3 is a schematic cross-sectional view of a third embodiment of the handpiece according to the invention; and, FIG. 4 is a schematic of isobars which emerge in the region of the needle tip during the use of the handpiece according to the invention.

FIG. 3 schematically shows a cross-section of a third embodiment of a front part of the handpiece according to the invention. A funnel-shaped region 207 with an opening zone 271 and an end 272 is embodied in such a way that an associated internal wall contour 210 has a free-form contour. If this free-form contour is embodied appropriately, there are no eddies, and so a high concentration of the energy emitted by the drive element 5 can be achieved in the direction toward the distal end 9 of the needle 10.

Figure 4:
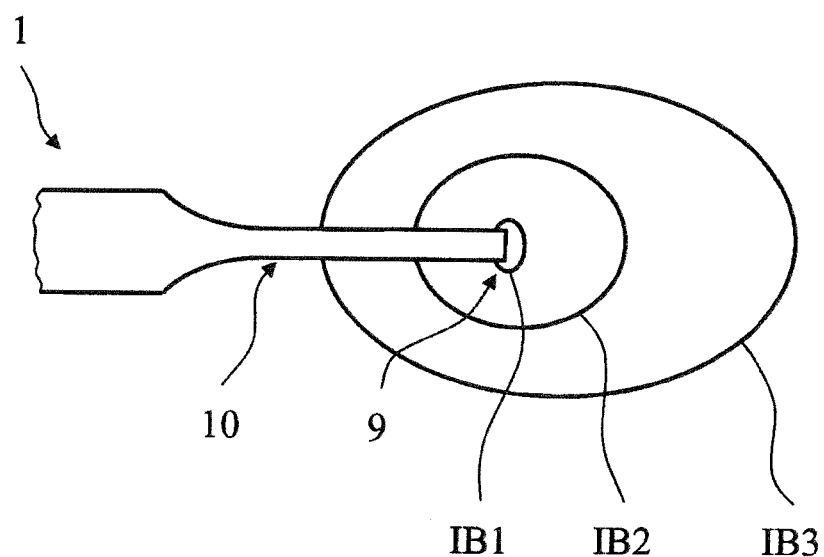

FIG. 4 depicts a needle 10 of the handpiece 1 according to the invention, wherein isobars (IB1, IB2, IB3) have additionally been plotted. When calculating the isobars, the following boundary conditions were considered:

Ultrasound wave speed in the aspiration fluid: $c_0=1484$ m/s

Ultrasonic frequency of the drive elements: $f_0=40\,000$ Hz;
Ultrasound wavelength in the aspiration fluid:
$l_0=c_0/f_0=37.1$ mm;
Amplitude of the drive elements: $a_0=50$ μm.

Taking into account these boundary conditions, a sound pressure level of IB1=276 dB emerges in the direct vicinity of the distal end 9 of the needle 10. This sound pressure level is directly applied onto the lens to be emulsified. At a distance of approximately 7 mm from the distal end 9 of the needle 10, there is a sound pressure level of approximately IB2=200 dB and a sound pressure level of approximately IB3=160 dB is prevalent at a distance of approximately 15 mm from the needle tip. The sound pressure level in the direct vicinity of the distal end 9 of the needle 10 in the case of the handpiece according to the invention reaches a value that is higher by approximately 50 dB than what can be reached in the case of a handpiece according to the prior art if the same boundary conditions are applied. This means that, in the handpiece according to the invention, a higher sound pressure level for emulsifying a lens of an eye can be generated with a stationary needle than what would be possible in the case of a vibrating needle in a conventional handpiece.

It is understood that the foregoing description is that of the preferred embodiments of the invention and that various changes and modifications may be made thereto without departing from the spirit and scope of the invention as defined in the appended claims.

LIST OF REFERENCE SIGNS

1 Handpiece in accordance with a first embodiment
2 Aspiration line
3 Aspiration fluid
4 Direction of the suctioning away
5 Drive element
51 Insulation of a drive element
6 Direction of the longitudinal movement
7 Funnel-shaped region
71 Opening zone of the funnel-shaped region 7
72 Tapered end of the funnel-shaped region 7
9 Distal end of the needle 10
10 Needle
11 Internal wall of the funnel-shaped region 7
12 Center of curvature of the internal wall 11
100 Handpiece in accordance with a second embodiment
107 Funnel-shaped region
110 Internal wall of the funnel-shaped region 107
120 Center of curvature of the second zone II of the funnel-shaped region 107
130 Center of curvature of the first zone I of the funnel-shaped region 107
171 Opening zone of the funnel-shaped region 107
172 Tapered end of the funnel-shaped region 107
200 Handpiece in accordance with a third embodiment
210 Internal wall
207 Funnel-shaped region
271 Opening zone of the funnel-shaped region 207
272 Tapered end of the funnel-shaped region 207
A Central axis of the aspiration line
L1 Length of the funnel-shaped region (7, 107, 207)
L2 Length of the needle 10
IB1, IB2, IB3 Isobars

What is claimed is:

1. A handpiece for effecting a phacoemulsification of an eye lens, the handpiece comprising:
    a needle;
    an aspiration line configured to transfer an aspiration fluid;
    said aspiration line being arranged within said needle;
    at least one drive element configured to vibrate and generate kinetic energy as a longitudinal wave; and,
    said at least one drive element being arranged so as to cause said longitudinal wave to be coupled directly into said aspiration fluid to impart a fluid pressure thereto to effect the phacoemulsification of the eye lens via said fluid pressure.

2. The handpiece of claim 1, wherein said at least one drive element is arranged within said aspiration line and in direct contact with the aspiration fluid.

3. The handpiece of claim 1, wherein said at least one drive element includes piezoelectric elements.

4. The handpiece of claim 1, wherein said at least one drive element has an annular shape.

5. The handpiece of claim 1, wherein:
    said needle has a distal end; and,
    said needle has a funnel-shaped region with a tapering end oriented toward said distal end.

6. The handpiece of claim 5, wherein:
    said aspiration line defines a center axis;
    said funnel-shaped region in cross section defines an inner wall contour; and,
    said inner wall contour is curved with respect to said center axis with a center of curvature in such a manner that said center of curvature is oriented toward said tapering end of said funnel-shaped region.

7. The handpiece of claim 1, wherein:
    said needle has a distal end; and,
    said distal end has an inner diameter lying in a range of 0.4 mm to 1.1 mm.

8. The handpiece of claim 1, wherein said needle has a distal end made of polymer plastic.

9. A handpiece for effecting a phacoemulsification of an eye lens, the handpiece defining a longitudinal axis and comprising:
- a needle;
- an aspiration line configured to transfer an aspiration fluid;
- said aspiration line being arranged within said needle;
- a drive element configured to generate movement energy in the direction of said longitudinal axis; and,
- said drive element being arranged so as to cause said movement energy to generate a longitudinal wave directly coupled only into said aspiration fluid to impart a fluid pressure thereto to effect the phacoemulsification of the eye lens via said fluid pressure while avoiding a transfer of kinetic energy to said needle which remains stationary during the phacoemulsification of the eye lens.

* * * * *